Nov. 1, 1966 R. S. MOORE Plant Pat. 2,682
ROSE PLANT
Filed Sept. 24, 1965
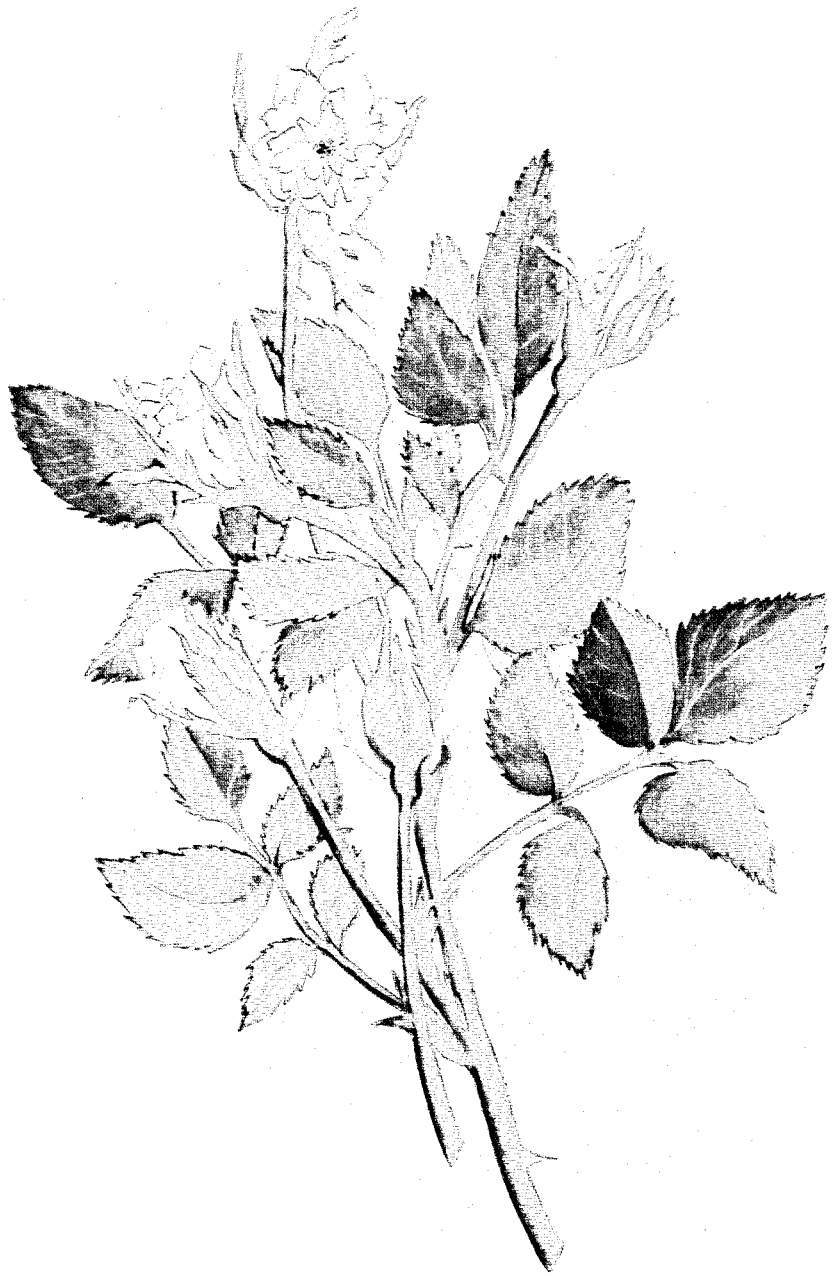
WITNESS
Jeanette Nunn Copley
INVENTOR
Ralph S. Moore United States Patent Office Plant Pat. 2,682
Patented Nov. 1, 1966

2,682
ROSE PLANT

Ralph S. Moore, 2519 E. Mineral King,
Visalia, Calif. 93277

Filed Sept. 24, 1965, Ser. No. 490,149
1 Claim. (Cl. Plt.—7)

The present invention relates to a new and distinct variety of hardy, drawf, bush type rose plant of the miniature class; the variety being primarily characterized—as to novelty—by bright yet soft orange-pink (sometimes near apricot color) buds and flowers which in general color effect are soft orange color.

The variety is further characterized by:

An abundance of bloom, with flowers borne singly or several to stem in loose clusters.

Moderate fragrance.

A plant which is vigorous, of rounded upright shape, and with semi-glossy, small foliage with pointed leaflets; the flowers and foliage being similar in size to the variety Tiny Jack (United States Plant Patent No. 2,484). The plant which has a normal average height of 10" to 14" at maturity can be easily maintained at 10" or less by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, California, under conditions of careful control and observation, as a cross between Little Darling (a floribunda rose, United States Plant Patent No. 1,581) as the seed parent, and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to he British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers:

*Continuity.*—Continuous.

*Fragrance.*—Moderate.

Flowers borne: Singly and several together (3 to 5) on normal strength medium length stems.

Quantity of bloom: Aundant both outside and in greenhouse.

Bud:

*Peduncle.*—Medium length; slender; erect; light green; few, very small short hairs. Before calyx breaks, size—small. Form long; pointed; with foliaceous appendages and numerous tiny short hairs on surface of the bud with foliaceous parts extending beyond the tip of the bud equal to one half or more of its length.

*Color.*—Medium green. As calyx breaks, color—orange to orange-pink. As first petal opens—same color, showing yellow at base of petal; size—small.

*Form.*—Medium length; pointed; becoming cupped as it opens.

*Opening.*—Opens well in all weather.

Bloom:

*Size when fully open.*—Small, averaging 1¼" to 1½".

*Petalage*—Double—35 petals (plus several narrow petaloids) arranged regularly.

*Form.*—Cupped at first, with petals rolled loosely outward, and later at maturity being loosely rolled outward with outer petals often rolled downward to give a ball effect.

Petals: Fairly thick; soft; satiny both inside and outside. Shape: Outside petals oval (broad lanceolate); intermediate—lanceolate; inside—narrow lanceolate.

Color: Newly opened flower from a plant grown outdoors (September 1965) Visalia, California.

*Outside petal.*—Outside surface—Shrimp Red 616/1 with yellow at base; inside surface—Azalea Pink 618 shading to yellow at base.

*Intermediate petal.*—Outside surface—Shrimp Red 616/1 with yellow at base; inside surface—Azalea Pink 618/1 shading into yellow at base.

*Inner petal.*—Outside surface—Shrimp Red 616/1 with yellow at base; inside surface—Azalea Pink 618/1 shading into yellow at base.

*General color effect newly opened flower.*—Apricot to orange. Three days open—soft pink.

*Behavior.*—Spent petals usually drop off. Flowers fade more quickly in warm weather.

*Flower longevity (September 1965).*—Bush in garden or pot—3 to 4 days. Cut flowers at living room temperature—2 to 3 days.

Reproductive organs:

*Stamens.*—Few to average; arranged irregularly about pistil, mixed with petaloids.

*Filaments.*—Short; yellow; anthers sometimes missing.

*Pollen.*—Scarce.

*Pistils.*—Few.

*Styles.*—Uneven; medium length; bunched.

*Stigma.*—Pale, greenish yellow.

*Ovaries.*—All enclosed in calyx.

*Hips.*—None.

*Sepals.*—Permanent; spear shaped; recurved.

*Seeds.*—None.

Foliage:

*Leaves.*—Compound of five leaflets; abundant; small to moderately small; leathery; semi-glossy to glossy.

*Leaflets.*—Shape—lanceolate; apex acute; base acute or rounded acute. Margin serrate. Color—normal green; new growth often tinted bronze. Rachis—medium strength; upper side smooth, grooved, smooth; under side sparsely thorny. Stipules—medium length; narrow; short to medium length points, turning out at an angle of less than 45 degrees.

Growth:

*Habit.*—Dwarf; bushy; rounded; much branched.

*Growth.*—Free; vigorous.

*Canes.*—Medium; slender.

*Main stems.*—Color—dull green. Thorns—moderately thorny; medium length; hooked slightly downward; color—medium brown. Prickles—none. Hairs—none.

*Branches.*—Color—medium green. Thorns—moderately thorny; short; hooked slightly downward; medium length oval base. Prickles—none. Hairs—none.

*New shoot.*—Color—medium green, often tinted bronze. Thorns — moderately thorny; short; hooked slightly downward; sharp points; base oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, dwarf, rounded, much branched, bush type, as illustrated and described, characterized by buds and flowers resembling the Little Scotch (Pat. 1,952) miniature rose in general form but with shorter bud length, the color orange to coral rather than straw yellow and flowers more cupped and slightly smaller; the general color effect being orange or apricot; and further characterized by a plant which is of vigorous and compact growth, easy to propagate from cuttings, with medium small semi-glossy foliage and an abundance of bloom, with flowers borne singly or several to stem in loose clusters.

No references cited.

ABRAHAM G. STONE, *Primary Examiner.*

R. E. BAGWILL, *Assistant Examiner.*